(12) United States Patent
Howard et al.

(10) Patent No.: US 6,727,223 B2
(45) Date of Patent: Apr. 27, 2004

(54) TREATMENT OF MICROBIAL INFECTIONS WITH BACTERIAL PROTEINS AND PEPTIDES

(75) Inventors: Jeffrey Howard, London (CA); Gregor Reid, London (CA); Bing Siang Gan, London (CA)

(73) Assignee: Urex Biotech, Inc., London (CA)

( * ) Notice: Subject to any disclaimer, the term of this patent is extended or adjusted under 35 U.S.C. 154(b) by 0 days.

(21) Appl. No.: 09/921,880

(22) Filed: Aug. 3, 2001

(65) Prior Publication Data

US 2002/0120101 A1 Aug. 29, 2002

Related U.S. Application Data

(60) Provisional application No. 60/223,065, filed on Aug. 4, 2000.

(51) Int. Cl.[7] .................. A01N 37/18; A61K 38/04
(52) U.S. Cl. .................. 514/2; 530/300; 530/328
(58) Field of Search .................. 435/69.1; 536/23.1; 514/2, 8; 530/300

(56) References Cited

U.S. PATENT DOCUMENTS 5,851,794 A * 12/1998 Guss et al. .............. 424/234.1
6,051,552 A * 4/2000 Reid et al. .............. 424/185.1

FOREIGN PATENT DOCUMENTS

WO        WO 92/03457        3/1992

OTHER PUBLICATIONS

Hook M, McGavin MJ, Switalski LM, Raja R, Raucci G, Lindgren PE, Lindgren M, Signas C. Interactions of bacteria with extracellular matrix proteins. Cell Differ Dev. Dec. 2, 1990;32(3):433–8.*
Rich R.L. et al., "Ace Is a Collagen–Binding MSCRAMM from *Enterococcus Faecalis*", *The Journal of Biological Chemistry* 274(38):26939–26945 (1999), XP002930358.

* cited by examiner

*Primary Examiner*—Karen Cochrane Carlson
*Assistant Examiner*—Sheridan Snedden
(74) *Attorney, Agent, or Firm*—Scully, Scott, Murphy & Presser (57) ABSTRACT

The present invention relates to protein and peptide chemistry. In particular, the present invention relates to the discovery and isolation of novel peptides whose sequences derive from microorganism by-products including biosurfactants. The invention is also directed to the use of these novel peptides in the inhibition of infections caused by pathogens.

5 Claims, 8 Drawing Sheets

(1 of 8 Drawing Sheet(s) Filed in Color)

SEQUENCE LISTING

<160> NUMBER OF SEQ ID NOS: 10

<210> SEQ ID NO 1
<211> LENGTH: 16
<212> TYPE: PRT
<213> ORGANISM: Lactobacillus fermentum
<220> FEATURE:
<221> NAME/KEY: UNSURE
<222> LOCATION: (1)
<223> OTHER INFORMATION: Xaa can be any amino acid
<221> NAME/KEY: UNSURE

```
<222> LOCATION: (4)
<223> OTHER INFORMATION: Xaa can be any amino acid
<221> NAME/KEY: UNSURE
<222> LOCATION: (7)..(8)
<223> OTHER INFORMATION: Xaa can be either Phe or Ala

<400> SEQUENCE: 1

Xaa Gln Gly Xaa Val Ser Xaa Xaa Gly Ser Cys Thr Cys Ala Gln Lys
 1               5                  10                  15

<210> SEQ ID NO 2
<211> LENGTH: 10
<212> TYPE: PRT
<213> ORGANISM: Lactobacillus fermentum
<220> FEATURE:
<221> NAME/KEY: UNSURE
<222> LOCATION: (4)
<223> OTHER INFORMATION: Xaa can be any amino acid
<221> NAME/KEY: UNSURE
<222> LOCATION: (8)..(9)
<223> OTHER INFORMATION: Xaa can be either Phe or Ala

<400> SEQUENCE: 2

Glu Val Tyr Xaa Phe Gln Glu Xaa Xaa Arg
 1               5                  10

<210> SEQ ID NO 3
<211> LENGTH: 5
<212> TYPE: PRT
<213> ORGANISM: Lactobacillus fermentum

<400> SEQUENCE: 3

Trp Asn Tyr Val Ser
 1               5

<210> SEQ ID NO 4
<211> LENGTH: 12
<212> TYPE: PRT
<213> ORGANISM: Lactobacillus fermentum
<220> FEATURE:
<221> NAME/KEY: UNSURE
<222> LOCATION: (5)..(6)
<223> OTHER INFORMATION: Xaa can be any amino acid

<400> SEQUENCE: 4

Arg Ala Phe Ala Xaa Xaa Ser Asn Trp Pro Val Lys
 1               5                  10

<210> SEQ ID NO 5
<211> LENGTH: 12
<212> TYPE: PRT
<213> ORGANISM: Lactobacillus fermentum
<220> FEATURE:
<221> NAME/KEY: UNSURE
<222> LOCATION: (2)
<223> OTHER INFORMATION: Xaa can be any amino acid
<221> NAME/KEY: UNSURE
<222> LOCATION: (4)..(5)
<223> OTHER INFORMATION: Xaa can be any amino aicd
<221> NAME/KEY: UNSURE
<222> LOCATION: (7)..(11)
<223> OTHER INFORMATION: Xaa can be either Ser or His

<400> SEQUENCE: 5

Gly Xaa Gln Xaa Xaa Asp Xaa Xaa Xaa Xaa Xaa Arg
 1               5                  10

<210> SEQ ID NO 6
<211> LENGTH: 11
<212> TYPE: PRT
```

```
<213> ORGANISM: Lactobacillus fermentum
<220> FEATURE:
<221> NAME/KEY: UNSURE
<222> LOCATION: (2)
<223> OTHER INFORMATION: Xaa can be any amino acid
<221> NAME/KEY: UNSURE
<222> LOCATION: (6)
<223> OTHER INFORMATION: Xaa can be any amino acid
<221> NAME/KEY: UNSURE
<222> LOCATION: (7)..(10)
<223> OTHER INFORMATION: Xaa can be either Ser or His

<400> SEQUENCE: 6

Gly Xaa Gln Asn Asp Xaa Xaa Xaa Xaa Xaa Arg
 1               5                  10

<210> SEQ ID NO 7
<211> LENGTH: 15
<212> TYPE: DNA
<213> ORGANISM: Staphylococcus aureus

<400> SEQUENCE: 7
gaagtcgtaa caagg                                                      15

<210> SEQ ID NO 8
<211> LENGTH: 15
<212> TYPE: DNA
<213> ORGANISM: Staphylococcus aureus

<400> SEQUENCE: 8
caaggcatcc accgt                                                      15

<210> SEQ ID NO 9
<211> LENGTH: 23
<212> TYPE: DNA
<213> ORGANISM: Lactobacillus fermentum

<400> SEQUENCE: 9
aaactttctt attctattct ggt                                             23

<210> SEQ ID NO 10
<211> LENGTH: 19
<212> TYPE: DNA
<213> ORGANISM: Lactobacillus fermentum

<400> SEQUENCE: 10
aactgattcg tcccgtaaa                                                  19
```

TREATMENT OF MICROBIAL INFECTIONS WITH BACTERIAL PROTEINS AND PEPTIDES

CROSS REFERENCE TO RELATED APPLICATION

This application claims priority from U.S. Provisional Application No. 60/223,065, filed Aug. 4, 2000.

FIELD OF THE INVENTION

The present invention relates to protein and peptide chemistry. In particular, the present invention relates to the discovery and isolation of novel peptides whose sequences derive from microorganism by-products including Lactobacillus biosurfactants. The invention is also directed to the use of these novel peptides in the inhibition of infections caused by pathogens.

BACKGROUND OF THE INVENTION

Microorganisms still represent one of the top three causes of death amongst humans and animals. The offending organisms can be bacteria, fungi, protozoa, viruses and other forms, collectively termed as pathogens (or organisms which behave like pathogens under certain situations, such as when the host is immunocompromised). Pathogens use many different factors to cause disease, including adhesins to colonize tissues and surfaces, toxins, slime and other capsular substances, antibiotic-resistance genes, immune modifiers and substances which help escape immune responses, etc.

The primary exogenous mechanism to eradicate offending pathogens is antimicrobial agents, such as antibiotics. However, these are often ineffective due to resistance of pathogenic organisms, inability to eradicate biofilms and poor penetration at the tissue or biomaterial interface.

There are a number of organisms which can infect the host. Of these, *S. aureus* (particularly methicillin-resistant—MRSA), *S. epidermidis* (particularly methicillin-resistant—MRSE), *Pseudomonas aeruginosa*, *Enterococcus faecalis* (including vancomycin-resistant—VRE) and *Bacteroides* sp. can be particularly detrimental in wounds and surgical implants. These and other aerobic and anaerobic pathogens cause severe morbidity and death in large patient populations.

Implanted medical devices, such as heart valves and artificial veins and joints, are especially vulnerable to microbial biofilm formation and disease (Gristina, (1987) *Science*, 237:1588–1595). These surfaces are not well protected by host defenses and such surfaces provide a focal point for infecting pathogens. Closed implants are more frequently associated with life-threatening morbidity. *Staphylococcus epidermidis* and *S. aureus* being the major pathogens associated with life-threatening infections (Christensen et al. (1989) "Microbial and foreign body factor in the pathogen of medical device infections. In infections associated with in dwelling medical devices", Bisno AL, Waldvogel FA (eds), ASM, Wash., pp. 2759). Thus, various microorganisms share a common ability to form biofilms and colonize human tissues in the presence and absence of foreign bodies.

To combat the significant infectious complication rates associated with the use of surgical implants, several strategies have been employed. Thus far, these have been mainly limited to:improved surgical asepsis techniques, improved regimens of administration of peri-operative systemic antibiotics, local antibiotic irrigation procedures, modification of surface characteristics of surgical implants and impregnation of surgical implants with antibiotics.

Thus, progress has been made, but that based on scientific innovation, has been relatively slow, and most citations in the literature still utilize traditional methods of management, such as use of antibiotics, antiseptics and surgical debridement. Newer approaches to prevent bacteria ascending towards clinical use include vacuum sealed and transparent film dressings, irrigation with antimicrobial agents, use of the port and cap, use of new agents such as deuteroporphyrin against *Staphylococcus aureus*, gamma interferon, silver sulfadiazone water soluble gel, geomagnetic therapy, and natural remedies such as milliacynic oil and lysozyme. However, few innovations have made a major impact on infection and fatality rates. Indeed, most new approaches involve delivery of an antimicrobial chemical, for example in liposomes or in collagen dressings.

SUMMARY OF THE INVENTION

One embodiment of the present invention is directed to microorganism biosurfactant peptides. In a preferred embodiment the microorganism is Lactobacillus. In another preferred embodiment the microorganism is *Staphylococcus epidermidis*. The present application also contemplates biosurfactant peptides isolated from Streptococcus sp., Bifidobacterium sp. and lactic acid bacteria. In accordance with the present invention, novel peptides derived from or corresponding to by-products produced by Lactobacilli have been isolated and synthesized. These peptides possess antimicrobial properties including the ability to selectively bind to collagen and inhibit infections around wounds and at the site of implants and biofilms which biofilms, for example, are associated with infections in mammals, in vivo. The peptides of the present invention are derived from human microorganism isolates and therefore are non-immunogenic, non-pathogenic, non-carcinogenic and non-invasive when administered to humans.

The present invention also provides methods and compositions for treating infections such as are commonly caused by *S. aureus* (particularly methicillin-resistant—MRSA), *S. epidermidis* (particularly methicillin-resistant—MRSE), *Pseudomonas aeruginosa*, *Enterococcus faecalis* (including vancomycin-resistant—VRE) and *Bacteroides* sp., for example.

The present invention also provides methods and compositions for coating devices, including stents, tubes, prosthetics, bandages, intravenous lines, catheters, diaphragms, tampons and the like. The present invention provides compositions containing at least one biosurfactant peptide which inhibits, prevents, treats or reduces the risk of infections in a mammal, and preferably humans.

The present invention also provides a method to identify proteins, peptides, glycoproteins and amino acid sequences from any given microorganism which block the lock and key adherence of pathogens, such as but not limited to Salmonella, Shigella, *E. coli*, Pseudomonas, Listeria, Yersinia, Enterococcus, Streptococcus and other pathogens including viruses and protozoa.

The biosurfactant peptides of the present invention are at least 5 amino acids in length and possess collagen-receptor binding activity. Collagen is a major extracellular matrix (ECM) component of tissues that has also been shown to be an important site of attachment for invading pathogenic bacteria, like *Staphylococcus aureus*.

A preferred biosurfactant peptide of the present invention is a peptide having the sequence $Xaa_1$-Gln-Gly-$Xaa_2$-Val- Ser-Xaa$_3$-Xaa$_4$-Gly-Ser-Cys-Thr-Cys-Ala-Gln-Lys (SEQ ID NO:1), wherein Xaa$_1$ and Xaa$_2$ can be any amino acid.

Preferably, Xaa$_1$, and Xaa$_2$ are Leu. Xaa$_3$ and Xaa$_4$ can either be Phe or Ala. Another preferred biosurfactant peptide of the present invention is a peptide having the sequence Glu-Val-Tyr-Xaa$_1$-Phe-Gln-Glu-Xaa$_2$-Xaa$_3$-Arg (SEQ ID NO:2), wherein Xaa$_1$ can be any amino acid and Xaa$_2$ and Xaa$_3$ can either be Gln or Pro. Another preferred biosurfactant peptide of the present invention is a peptide having the sequence Trp-Asn-Tyr-Val-Ser (SEQ ID NO:3). Still another preferred biosurfactant peptide of the present invention is a peptide having the sequence Arg-Ala-Phe-Ala-Xaa$_1$-Xaa$_2$-Ser-Asn-Trp-Pro-Val-Lys (SEQ ID NO:4), wherein Xaa$_1$ and Xaa$_2$ can be any amino acid. Yet another preferred biosurfactant peptide of the present invention is a peptide having the sequence Gly-Xaa$_1$-Gln-Xaa$_2$-Xaa$_3$-Asp-Xaa$_4$-Xaa$_5$-Xaa$_6$-Xaa$_7$-Xaa$_8$-Arg (SEQ ID NO: 5), wherein Xaa$_1$, Xaa$_2$, Xaa$_3$ and Xaa$_4$ can be any amino acid and Xaa$_5$, Xaa$_6$, Xaa$_7$, and Xaa$_8$ can be either Ser or His. Homologs and analogs of these peptides are also contemplated by the present invention.

Further, according to the present invention a biosurfactant peptide can be at least 5 amino acids and composed of up to a full length biosurfactant protein, as long as the peptide binds to a collagen receptor and possesses anti-pathogenic activity.

Another aspect of the present invention provides methods of interfering with, blocking or otherwise preventing the interaction or binding of microbial pathogens to collagen receptors on cells, for example, by employing the biosurfactant peptides contemplated by the present invention. As such the present peptides are understood to act as microbial antagonists.

Another aspect of the present invention provides methods of interfering with blocking or otherwise preventing the interaction or binding of microbial pathogens to extracellular matrix substances on cells or on the outer surface conditioning film of a biomaterial, for example.

The present invention also provides compositions for the treatment of infections such as occur at wound sites, implant sites and the like in animals, including humans and includes methods of treating such disorders. The compositions include at least one of the biosurfactant peptides, preferably at least the biosurfactant peptide according to the present invention, is admixed with a pharmaceutically acceptable carrier.

Nucleic acid molecules coding for any of the above biosurfactant peptides of the present invention, expression vectors which include any of such nucleic acid molecules, as well as related host cells containing such nucleotide sequences or vectors, are also contemplated by the present invention.

These and other embodiments of the invention will be readily apparent to those of ordinary skill in view of the disclosure herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

The present invention is directed to biosurfactant peptides. In a preferred embodiment the peptides are isolated from Lactobacillus biosurfactants. The present invention also contemplates peptides isolated from Staphylococcus sp., Streptococcus sp., Bifidobacterium sp. and lactic acid bacteria. As defined by the present invention, a biosurfactant is a compound released by microorganisms with a tendency to accumulate at interfaces, most notably the liquid-air interface. By "biosurfactant peptides" is meant any molecule that inhibits, prevents, treats or reduces the risk of infections around wounds and at the site of biologically compatible implants by, e.g., interfering with, blocking the receptors onto which pathogens would otherwise bind including cells and biologically compatible devices. As used herein a "biologically compatible device" may be composed of polymers such as fluorinated ethylene propylene, sulfonated polystyrene, polystyrene, polyethyleneterephthalate silicone, polyurethane, polyvinylchloride silicone rubber, or glass, for example. The biodevice may be a catheter such as a urinary or peritoneal catheter, a diaphragm, a stent, an IUD or a diaper, an intravenous line, a peritoneal dialysis tube, a bandage, an endotracheal tube, or an intravaginal, intrauterine, or intraurethral or intraurethral device, for example.

As used herein, "peptide" refers to a linear series of amino acid residues linked to one another by peptide bonds between the alpha-amino and carboxy groups of adjacent amino acid residues. The term "synthetic peptide" is intended to refer to a chemically derived chain of amino acid residues linked together by peptide bonds. The term "synthetic peptide" is also intended to refer to recombinantly produced peptides in accordance with the present invention.

The sequences of the peptides of the present invention are isolated from a biosurfactant, e.g., Lactobacillus. A preferred Lactobacillus is L. fermentum RC-14. However, peptide analogs derived from other Lactobacilli, including but not limited to L. rhamnosus GR-1 and other microorganisms are also encompassed by the invention. In the practice of the compositions and methods of the present invention, the biosurfactant peptides may be isolated from any microorganisms, in particular Lactobacillus species, especially *L. fermentum, L. acidophilus, L. reuteri*, but also potentially also *L. rhamnosus, L. casei, L. crispatus, L. plantarum, L. paracasei, L. jensenii, L. gasseri, L. cellobiosis, L. brevis, L. delbrueckii, L. helveticus, L. salivarius, L. collinoides, L. buchneri, L. rogosae,* and *L. bifidum.* These proteins can also be isolated from Staphylococcus sp., Bifidobacterium sp. and other organisms.

A biosurfactant peptide functions in at least two ways. While not wishing to be bound to a particular mechanism of action, the peptides of the present invention can bind to or sequester collagen receptors with sufficient affinity and specificity to substantially interfere with, block or otherwise prevent binding of pathogens, thereby inhibiting or preventing infections. Alternatively, a biosurfactant peptide can act as a signaling molecule which can turn off a pathogen's virulence capability, thereby also inhibiting or preventing infections. Additionally, analogs, and fragments of the novel peptides provided herein are included within the scope of the term "biosurfactant peptide".

By "analogs" is meant peptides which differ by one or more amino acid alterations, which alterations, e.g., substitutions, additions or deletions of amino acid residues, do not abolish the anti-pathogenic properties of the relevant peptides.

Thus, an analog may comprise a peptide having a substantially identical amino acid sequence to a peptide provided herein and in which one or more amino acid residues have been conservatively or non-conservatively substituted. Examples of conservative substitutions include the substitution of a non-polar (hydrophobic) residue such as isoleucine, valine, leucine or methionine for another. Likewise, the present invention contemplates the substitution of one polar (hydrophilic) residue such as between arginine and lysine, between glutamine and asparagine, and between glycine and serine. Additionally, the substitution of a basic residue such as lysine, arginine or histidine for another or the substitution of one acidic residue such as aspartic acid or glutamic acid for another is also contemplated. Examples of non-conservative substitutions include the substitution of a non-polar (hydrophobic) residue such as isoleucine, valine, leucine, alanine, methionine for a polar (hydrophilic) residues such as cysteine, glutamine, glutamic acid, lysine and/or a polar residue for a non-polar residue.

The phrase "conservative substitution" also includes the use of chemically derivatized residues in place of a non-derivatized residues as long as the peptide retains the requisite anti-microbial activity.

Analogs also include the presence of additional amino acids or the deletion of one or more amino acids which do not affect biological activity. In addition, for purposes of the present invention, peptides containing D-amino acids in place of L-amino acids are also included in the term "conservative substitution."

A preferred biosurfactant peptide of the present invention is a peptide having the sequence $Xaa_1$-Gln-Gly-$Xaa_2$-Val-Ser-$Xaa_3$-$Xaa_4$-Gly-Ser-Cys-Thr-Cys-Ala-Gln-Lys (SEQ ID NO:1), wherein $Xaa_1$ and $Xaa_2$ can be any amino acid. Preferably, $Xaa_1$ and $Xaa_2$ are Leu. $Xaa_3$ and $Xaa_4$ can either be Phe or Ala. Another preferred biosurfactant peptide of the present invention is a peptide having the sequence Glu-Val-Tyr-$Xaa_1$-Phe-Gln-Glu-$Xaa_2$-$Xaa_3$-Arg (SEQ ID NO:2), wherein $Xaa_1$, can be any amino acid and $Xaa_2$ and $Xaa_3$ can either be Gln or Pro. Another preferred biosurfactant peptide of the present invention is a peptide having the sequence Trp-Asn-Tyr-Val-Ser (SEQ ID NO:3). Still another preferred biosurfactant peptide of the present invention is a peptide having the sequence Arg-Ala-Phe-Ala-$Xaa_1$-$Xaa_2$-Ser-Asn-Trp-Pro-Val-Lys (SEQ ID NO:4), wherein $Xaa_1$ and $Xaa_2$ can be any amino acid. Yet another preferred biosurfactant peptide of the present invention is a peptide having the sequence Gly-$Xaa_1$-Gln-$Xaa_2$-$Xaa_3$-Asp-$Xaa_4$-$Xaa_5$-$Xaa_6$-Xaa7-$Xaa_8$-Arg (SEQ ID NO: 5), wherein $Xaa_1$, $Xaa_2$, $Xaa_3$ and $Xaa_4$ can be any amino acid and $Xaa_5$, $Xaa_6$, $Xaa_7$, and $Xaa_8$ can be either Ser or His. Still yet another preferred biosurfactant peptide of the present invention is a peptide having the sequence Gly-$Xaa_1$-Gln-Asn-Asp-$Xaa_2$-$Xaa_3$-$Xaa_4$-$Xaa_5$-$Xaa_6$-Arg (SEQ ID NO:6), wherein $Xaa_1$ and $Xaa_2$ can be any amino acid and $Xaa_3$ $Xaa_4$, $Xaa_5$ and $Xaa_6$ can be either Ser or His. The phrase "any amino acid" is understood, in accordance with the present application to include:

A=Ala=Alanine

R=Arg=Arginine

N=Asn=Asparagine

D=Asp=Aspartic acid

B=Asx=Asparagine or aspartic acid

C=Cys=Cysteine

Q=Gln=Glutamine

E=Glu=Glutamic acid

Z=Glx=Glutamine or Glutamic acid

G=Gly=Glycine

H=His=Histidine

I =Ile=Isoleucine

L=Leu=Leucine

K=Lys=Lysine

F=Phe=Phenylalanine

P=Pro=Proline

S=Ser=Serine

T=Thr=Threonine

W=Trp=Tryptophan

Y=Tyr=Tyrosine

V=Val=Valine

Further, according to the present invention a biosurfactant peptide can be longer than 5 amino acids and composed of up to a full length biosurfactant protein.

As used herein, the term "substantially corresponds" is meant the degree of amino acid homology of at least about 60% homology, preferably at least about 70%, and more preferably at least about 75%, which degree is the similarity index calculated using the Lipman-Pearson Protein Alignment program with the following choice of parameters: Ktuple=2, Gap penalty=4, and Gap Length Penalty=12.

The term "fragment" refers to any subject peptide having an amino acid sequence shorter than that of any peptide depicted in SEQ ID NOS: 1–6 and which fragment retains the anti-pathogenic activity of the subject peptides.

The practice of the present invention employs, unless otherwise indicated, conventional techniques of synthetic organic chemistry, protein chemistry, molecular biology, microbiology, and recombinant DNA technology, which are well within the skill of the art. These techniques are applied in connection with peptide identification, synthesis, recombinant production of peptides and peptide mutagenesis, for example. Such techniques are explained fully in the literature. See e.g., Scopes, R. K., *Protein Purification Principles and Practices,* 2d ed. (Springer-Verlag. 1987), *Methods in Enzymology* (M. Deutscher, ed., Academic Press, Inc. 1990), Sambrook, et al., *Molecular Cloning: A laboratory Manual,*

2d ed., (Cold Spring Harbor Press, Cold Spring Harbor, N.Y., 1989), *Handbook of Experimental Immunology*, Vols. I–IV (D. M. Weir and C. C. Blackwell, eds., 1986, Blackwell Scientific Publications), House, *Modern Synthetic Reactions,* 2d ed., (Benjamin/Cummings, Menlo Park, Calif., 1972).

The peptides of the present invention are screened within the biosurfactant, e.g. RC-14, using Surface Enhanced Laser Desorption/Ionization time of flight mass spectrometry (SELDI-TOF-MS). The peptides of the present invention, analogs and fragments thereof may be synthesized by a number of known techniques. For example, the peptides may be prepared using the solid-phase synthetic technique initially described by Merrifield, in *J. Am. Chem. Soc.* 85:2149–2154 (1963). Other peptide synthesis techniques may be found in M. Bodanszky, et al. *Peptide Synthesis*, John Wiley & Sons, 2d Ed., (1976) and other references readily available to those skilled in the art. A summary of polypeptide synthesis techniques can be found in J. Stuart and J. D. Young, *Solid Phase Peptide Synthesis*, Pierce Chemical Company, Rockford, Ill., (1984). Peptides may also be synthesized by solution methods as described in *The Proteins,* Vol. II. 3d Ed., Neurath, H. et al., Eds., p. 105–237, Academic Press, New York, N.Y. (1976). Appropriate protective groups for use in different peptide syntheses are described in the above-mentioned texts as well as in J. F. W. McOmie, *Protective Groups in Organic Chemistry*, Plenum Press, New York, N.Y. (1973).

Additionally, the peptides of the present invention may also be prepared by recombinant DNA techniques (see e.g. *Current Protocols in Molecular Cloning* Ausubel et al., 1995, John Wiley & Sons, New York); Sambrook et al., 1989, *Molecular Cloning: A Laboratory Manual,* Second Edition, Cold Spring Harbor Laboratory Press, New York; Coligan et al. *Current Protocols in Immunology*, John Wiley & Sons Inc., New York, N.Y. (1994)). The skilled artisan understands that any of a wide variety of expression systems can be used to provide the recombinant peptides of the present invention. The precise host cell used is not critical to the invention. The biosurfactant peptides can be produced in a prokaryotic host (e.g. *E. coli*), or in a eukaryotic host (e.g., *S. cerevisiae* or mammalian cells, e.g. COS1, CHO, NIH3T3, and JEG3 cells, or in the cells of an arthropod, e.g. *S. frugiperda*). Such cells are available from e.g. the American Type Culture Collection, Manassas, Va. The method of transfection and the choice of expression vehicle will depend on the host system selected. Transformation and transfection methods are described, e.g. in Sambrook et al. supra; expression vehicles can be chosen from those provided e.g. in *Cloning Vectors: A Laboratory Manual* P. H. Powels et al (1985), Supp. 1987.

For most of the amino acids used to build proteins, more than one coding nucleotide triplet (codon) can code for a particular amino acid residue. This property of the genetic code is known as redundancy. Therefore, a number of different nucleotide sequences can code for a particular subject biosurfactant peptide e.g., Lactobacillus biosurfacnt peptide. The present invention also contemplates a deoxyribonucleic acid (DNA) molecule or segment that defines a gene coding for, i.e., capable of expressing, a subject peptide or a subject chimeric peptide from which a peptide of the present invention may be enzymatically or chemically cleaved.

DNA molecules that encode peptides of the present invention can be synthesized by chemical techniques, for example, the phosphotriester method of Matteuccie, et al., *J. Am. Chem. Soc.* 103:3185(1981). Using a chemical DNA synthesis technique, desired modifications in the peptide sequence can be made by making substitutions for bases which code for the native amino acid sequence. Ribonucleic acid equivalents of the above described DNA molecules may also be used.

A nucleic acid molecule comprising a vector capable of replication and expression of a DNA molecule defining coding sequence for a subject polypeptide or subject chimeric polypeptide is also contemplated.

The peptides of the present invention are chemically synthesized by conventional techniques such as the Merrifield solid phase technique. In general, the method comprises the sequential addition of one or more amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine.

A preferred method of solid phase synthesis entails attaching the protected or derivatized amino acid to an inert solid support through its unprotected carboxyl or amino group. The protecting group of the amino or carboxyl group is then selectively removed and the next amino acid in the sequence having the complementary (amino or carboxyl) group suitably protected is admixed and reacted under conditions suitable for forming the amide linkage with the residue already attached to the solid support. The protecting group of the amino carboxyl group is then removed from this newly added amino acid residue, and the next amino acid (suitably protected) is then added, and so forth. After all the desired amino acids have been linked in the proper sequence, any remaining terminal and side group protecting groups including the solid support are removed sequentially or concurrently to yield the final peptide. The lyophilized oligopeptides are resuspended in double distilled $H_2O$ at 2 mg/ml as stock solutions and subsequently diluted in M199-HPS for experiments.

Peptides SEQ ID NOS:1–6 have the following sequences:

SEQ ID NO:1 $Xaa_1$-Q-G-$Xaa_2$-V-S-$Xaa_3$-$Xaa_4$-G-S-C-T-C-A-Q-K

SEQ ID NO:2 E-V-Y-$Xaa_1$-F-Q-E-$Xaa_2$-$Xaa_3$-R

SEQ ID NO:3 W-N-Y-V-S

SEQ ID NO:4 R-A-F-A-$Xaa_1$-$Xaa_2$-S-N-W-P-V-K

SEQ ID NO:5 G-$Xaa_1$-Q-$Xaa_2$-$Xaa_3$-D-$Xaa_4$-$Xaa_5$-$Xaa_6$-$Xaa_7$-$Xaa_8$-R

SEQ ID NO:6 G-$Xaa_1$-Q-N-D-$Xaa_2$-$Xaa_3$-$Xaa_4$-$Xaa_5$-$Xaa_6$-R including analogs and fragments which maintain anti-pathogen activity; wherein A=Ala=Alanine R=Arg=Arginine N=Asn=Asparagine D=Asp=Aspartic acid B=Asx=Asparagine or aspartic acid C=Cys=Cysteine Q=Gln=Glutamine E=Glu=Glutamic acid Z=Glx=Glutamine or Glutamic acid G=Gly=Glycine H=His=Histidine I=Ile=Isoleucine L=Leu=Leucine K=Lys=Lysine F=Phe=Phenylalanine
P=Pro=Proline
S=Ser=Serine
T=Thr=Threonine
W=Trp=Tryptophan
Y =Tyr=Tyrosine
V=Val=Valine
X=$Xaa_1$=Any amino acid Consistent with the observed properties of the peptides of the invention, the present peptides can be used to inhibit, prevent, treat or reduce the risk of pathogen-induced infection in animals, including humans. Organisms which can infect the host, including *S. aureus* (particularly methicillin-resistant—MRSA), *S. epidermidis* (particularly methicillin-resistant—MRSE) *Pseudomonas aeruginosa, Enterococcus faecalis* (including vancomycin-resistant—VRE), Bacteroides sp. and certain viruses bind to collagen receptors and thus can be particularly detrimental in wounds and surgical implants. Accordingly, the present invention contemplates methods to block, interrupt or otherwise prevent the association of pathogenic organisms to collagen receptors and thereby effectively inhibit, prevent and/or treat infections.

In another embodiment, the peptides of the present invention can be provided in consumer products such as cellophane wraps, sandwich bags, bottle tops, food preparation trays to block or inhibit pathogens from binding to the polymers or materials used to manufacture such consumer products.

In still another embodiment, beneficial flora from a subject suffering from an infection is identified and by products produced therefrom are detected and proteins or peptides are then isolated from the by-products, e.g., biosurfactants. The proteins or peptides isolated from the by-products are e.g., exogenously applied to the subject to reduce the risk of infection and to eradicate or inhibit such infection.

In still yet another embodiment of this invention, a diagnostic system is provided which identifies organisms within a subject, which organisms express proteins, peptides, glycoproteins or amino acids which function as blockers or inhibitors of pathogen binding. The diagnostic system used to identify the desired indigenous microorganisms includes singly or in combination SELDI (protein ID), molecular typing, PCR and other conventional tools. For example, a strain of *Staphylococcus epidermidis* present on the skin of a subject or Lactobacillus in the intestine of a subject which expresses a desired protein is detected in accordance with the present invention. Prebiotics (nutrients which stimulate the normal flora but do not stimulate pathogens), functional foods or other substances, are introduced to enhance the presence of the strain which produces the blocking substances, e.g., peptides and in this way reduces the risk of pathogenic infection in the host.

If the patient is susceptible to infection by various pathogens, such as multi-drug resistant staphylococci, vancomycin resistant enterococci and Klebsiella, a combination of blocking proteins, peptides, glycoproteins or amino acids is introduced to confer protection. The present invention also contemplates stimulation of the normal flora in the intestine (a common source of infecting organisms), vagina, oral cavity, respiratory tract, skin or other sites.

In another embodiment of the present invention, one or more biosurfactant peptides are included in pharmaceutical compositions.

Preferably, compositions containing the biosurfactant peptides of the present invention are administered topically (i.e. directly to the site of a wound or the skin, tissue or medical biologically compatible devices), as a spray, as an integral part of a bandage, as an adjunct to antibiotic or antiviral or antifungal therapy or in liposomes or other delivery vehicles, or intravaginally, intrarectally, orally or intravenously to inhibit, prevent or treat infection. When administered intravenously, the peptide compositions may be combined with other ingredients, such as carriers and/or adjuvants. The peptides may also be covalently attached to a protein carrier, such as albumin, so as to minimize clearing of the peptides. There are no limitations on the nature of the other ingredients, except that such ingredients must be pharmaceutically acceptable, efficacious for their intended administration and cannot degrade the activity of the active ingredients of the compositions. Pharmaceutical compositions containing the biosurfactant peptides suitable for oral administration may be incorporated in foods or nutrients ingested to interfere with pathogen colonization and spread in the gut.

The pharmaceutical forms suitable for injection include sterile aqueous solutions or dispersions and sterile powders for the extemporaneous preparation of sterile injectable solutions or dispersions. In all cases the ultimate solution form must be sterile and fluid. Typical carriers include a solvent or dispersion medium containing, for example, water buffered aqueous solutions (i.e., biocompatible buffers), ethanol, polyols such as glycerol, propylene glycol, polyethylene glycol, suitable mixtures thereof, or vegetable oils. Sterilization can be accomplished by any art-recognized technique, including but not limited to, filtration or addition of antibacterial or antifungal agents, for example, paraben, chlorobutanol, phenol, sorbic acid or thimerosal. Further, isotonic agents such as sugars or sodium chloride may be incorporated in the subject compositions.

Production of sterile injectable solutions containing the subject peptides is accomplished by incorporating these compounds in the required amount in the appropriate solvent with various ingredients enumerated above, as required, followed by sterilization, preferably filter sterilization. To obtain a sterile powder, the above solutions are vacuum-dried or freeze-dried as necessary.

When the peptides of the invention are administered orally, the pharmaceutical compositions thereof containing an effective dose of the peptide can also contain an inert diluent, as assimilable edible carrier and the like, be in hard or soft shell gelatin capsules, be compressed into tablets, or may be in an elixir, suspension, syrup or the like.

The subject peptides are thus compounded for convenient and effective administration in pharmaceutically effective amounts with a suitable pharmaceutically acceptable carrier in a therapeutically effective dose.

The peptides should preferably be administered in an amount of at least about 100 ng per dose, more preferably in an amount up to about 5 mg to about 2 grams per dose. Since the peptide compositions of this invention will eventually be cleared from the bloodstream, re-administration of the compositions is indicated and preferred.

The peptides can be administered in a manner compatible with the dosage formulation and in such amount as well be therapeutically effective. Systemic dosages depend on the age, weight and conditions of the patient and on the administration route. For example, a suitable dose for the administration to adult humans ranges from about 5 mg to about 2 g per kilogram of body weight.

As used herein, a pharmaceutically acceptable carrier includes any and all solvents, dispersion media, coatings, antibacterial and antifungal agents, isotonic agents the like. The use of such media and agents are well-known in the art.

The pharmaceutically acceptable carriers used in conjunction with the peptides of the present invention vary according to the mode of administration. For example, the compositions may be formulated in any suitable carrier for oral liquid formulation such as suspensions, elixirs and solutions. Compositions for liquid oral dosage include any of the usual pharmaceutical media such as, for example, water, skim milk, yogurt, oils, alcohols, flavoring agents, preservatives, coloring agents and the like. In the case of oral solid preparations (capsules and tablets) carriers such as starches, sugars, diluents, granulating agents, lubricants, binders, disintegrating agents and the like may be used. In addition, carriers such as liposomes and microemulsions may be used.

In a further aspect of the present invention, the pharmaceutical compositions of the present invention are employed for the treatment of infection. Thus, the present invention provides methods of treating an infection in a subject by administering a therapeutically effective amount of a pharmaceutical composition of the present invention.

The term "therapeutically effective amount" means the dose required to treat an infection.

By "infection" is meant a pathological disorder, the onset, progression or the persistence of the symptoms of which requires the participation of one or more biosurfactant peptides.

The term "treatment" or "treat" refers to effective inhibition, prevention or treatment of the infection.

The term "subject" refers to any mammalian subject. Preferably, the subject is a human.

The invention is further illustrated by the following specific examples which are not intended in any way to limit the scope of the invention.

EXAMPLE 1

SELDI (surface enhanced laser desorption/ionization) was used to separate, detect and analyze native proteins without using labeling or time consuming biochemical analytical systems. The SELDI system was used to quickly and accurately determine whether clinically important strains of lactobacilli expressed collagen binding proteins.

Four Lactobacillus strains were tested. *L. fermentum* RC-14 was selected because of its potent biosurfactant inhibitory activity against many pathogens. *L. rhamnosus* GR-1 and 36 also produce biosurfactants, and were also inhibitory to enterococci.

The organisms were grown in MRS broth overnight, harvested and the biosurfactant isolated by incubating the organisms for two hours at room temperature.

EXAMPLE 2

Animal Housing

Eight week-old (300 gram) male Sprague-Dawley rats (Charles River Inc, Montreal QC) were housed in shoebox plastic cages (2 animals per cage), maintained on a 12-hour light cycle, and given free access to standard rodent chow and water. Following surgery, the animals were examined daily for clinical signs of infection.

Bacterial Cultures

*Staphylococcus aureus* (Oxford strain) was cultured in Brain Heart (BH) growth media overnight at 37° C. and plated on BH agar plates to determine the colony-forming unit (CFU) activity of the bacteria. Following CFU measurements *S. aureus* (SA) suspensions were diluted in phosphate buffered saline (PBS) to attain the correct number of CFU for subsequent surgical implant inoculation in vivo. In a similar procedure, *Lactobacillus fermentum* RC-14 and *Lactobacillus rhamnosus* GR-1 were cultured using MRS Broth and MRS agar plates. CFU measurements were taken and appropriate PBS dilutions prepared for surgical implant inoculations in vivo.

Biosurfactant Production and Isolation from *Lactobacillus fexmentum* RC-14 cultures Crude biosurfactant (BSF) was collected from lactobacilli strains GR-1 and RC-14 as previously described (Reid, G., C. Heinemann, M. Velraeds, H. C. van der Mei, and H. J. Busscher. 1999. Biosurfactants produced by Lactobacillus. Methods in Enzymol. 310: 426–432, incorporated herein by reference). Bacterial cells were harvested by centrifugation (10,000×g, 10 min, 10° C.), washed twice in demineralized water and re-suspended in PBS. The Lactobacilli were then placed at room temperature and gently stirred for 2 hr to trigger the release of the biosurfactant. The solution was then centrifuged (10,000×g, 10 min, 10° C.), and the supernatant collected, filtered (0.22 mm) and dialyzed against double demineralized water at 4° C., using spectrapor dialysis tubing (6–8 kDa MW cutoff). The dialyzed substance was either used directly or freeze-dried (−10° C./−5 uM Hg/1–2 days) and stored at −20° C. Protein concentrations were determined using a BCA protein assay kit (Pierce). For surgical implant experiments the biosurfactant was suspended in sterile PBS (2 mg/ml) and incubated with the surgical implants for 12 hours at 4° C. prior to placing them in the animals.

Animal Surgery

Sprague-Dawley rats were anaesthetized via peritoneal injection of a mixture of hydrochloride-ketamine (100 mg/ml) and xylazine (10 mg/ml) at the rate of 0.1 ml per 100 g of body weight. Each anaesthetized rat was clipped of dorsal hair at the surgical site and liberally swabbed with a povi-iodine antiseptic solution. A single 2 cm incision was made along the dorsal skin. A single (1 cm×1 cm×0.5 mm) sterile silicone implant (Dagnone Inc.) was then inserted into the subcutaneous pocket adjacent to the skin incision and co-inoculated with the indicated number of *S. aurues* CFU (FIG. 1) and the indicated amount of either RC-14 biosurfactant peptides, bovine serum albumin (BSA), or recombinant His-tagged p29CnB. Surgical incisions were then closed with 3.0 polygalactin-coated 910 (vicryl) interrupted sutures and animals treated with post-operative analgesic (buprenorphine hydrochloride, 0.01 mg/kg subcutaneously).

*S. aureus* CFU Measurements from Surgical Implants

At the specified post-operative times, animals were sacrificed by $CO_2$ asphyxiation. Surgical sites were opened and immediately assessed for signs of acute inflammation and infection. Silicone implants and the surrounding tissues were harvested. Wound fluid was also collected from infected surgical sites and stored at −80° C. Surgical implant associated bacteria were harvested by sonication and bacterial numbers quantified using standard microbiological techniques. Implants were rinsed in PBS and then subjected to a 30-second sonication treatment. PBS diluted bacterial suspensions were then plated on either MRS (lactobacilli), or BH (*S. aureus*) agar plates and incubated overnight at 37° C. under anaerobic (5% $CO_2$) or aerobic conditions, respectively.

Gram Staining of Implants

Harvested implants were analyzed using a Gram staining kit (CMS protocol, Fisher) in order to assess both the extent of bacterial colonization of the implants and the efficiency of harvesting the implant adherent bacteria by sonication. The staining procedure included: Crystal violet (1 min), iodine solution (1 min), decolorizing agent (30 sec), safranin (1 min). Implants were then imaged using a light microscope (Axiophot, Zeiss).

Polymerase Chain Reaction (PCR)

The PCR technique was used to verify the species of bacteria obtained from each surgical implant. Briefly, bacteria colonies were picked, briefly washed in a Tris-EDTA buffer (pH 7.4), lysed in 10% SDS for 30 mm. centrifuged (4000 rpm, 5 min) and the resulting pellet heated in a 300 Watt-microwave (Hi power) for 5 minutes. DNA was isolated from each pellet via phenol/chloroform/isoamyl alcohol (24:23:1) (pH 8.0) extraction (1×), followed by ethanol precipitated. The DNA was then added to a PCR reaction mixture containing: 0.5 mM specific oligo-nucleotide primers (*Staphylococcus aureus* forward primer=5'-GAAGTCGTAACAAGG-3' (SEQ ID NO:7) and reverse primer=5'-CAAGGCATCCACC GT-3' (SEQ ID NO:8); *L. fermentum* RC-14 forward primer=5'-AAACTTTCTTAT-TCTATTCT GGT-3' (SEQ ID NO:9) and reverse primer= 5'-AACTGATTCGTCCCGTAAA-3' (SEQ ID NO:10); *L. rhamnosus* GR-1 forward primer=5'-ACGAGGC AC-3', reverse primer=5'-ACGCGCCCT-3'), 0.3 mM dNTP, 2 mM $MgCl_2$, and 1 unit of Platinum Taq Polymerase (Gibco-BRL) in a final reaction volume of 50 ml. PCR thermal cycling (Model 212 Lab-line) parameters included: 1 denaturation cycle (2 min/94° C.), followed by either 25 amplification cycles (denaturation 1 min/94° C., annealing 7 min/52° C., and extension 2 min/68° C.) for *S. aureus*, or 40 amplification cycles (denaturation 1 min/94° C., annealing 2 min/52° C. or 35° C. and extension 2 min/68° C.) for RC-14 and GR-1 respectively. This was followed by a final extension cycle of 10 min at 68° C. The PCR products were separated by agarose (2%) gel electrophoresis, visualized by ethidium bromide staining and photographed under UV transillumination.

Isolation of Collagen-binding Proteins from *L. fermentum* RC-14 Using Collagen Affinity Columns

*Lactobacillus ferementum* RC-14 biosurfactant (4 mg) was applied to either a collagen type-I (rat tail, Sigma) or collagen type-III (bovine skin, Sigma) polystyrene alkylamine bead affinity column as per the manufacturers advice (Pierce). Briefly, 100 hydrazide derivatized ¼ inch diameter spherical polystyrene beads (Pierce), were soaked in 50 mM phosphate buffer (pH 6.0) containing 10 gm of succinic anhydride for 15 hr at room temperature. The beads were then washed extensively in distilled water and then treated with a XmM EDC (1-Ethyl,3,3-dimethylaminopropyl-carbodiimide HCl) solution (pH 10) 2 hours at room temperature. The beads were then washed with distilled water and then incubated overnight at 4° C. with a PBS solution containing 5 mg (total) of either Collagen I or Collagen III. The beads were then packed into a 30 cc syringe column and then equilibrated with a 3 bed volumes of PBS (pH 7.4). Biosurfactant (4 mg) was applied to the column and the resulting flow-through re-applied (5×) to allow for optimal protein binding. Flow-though fractions were then collected and the column washed with 2 bed volumes of PBS. Bound proteins were then eluted with a PBS solution containing 1 M NaCl fractions. All fractions were analyzed for protein concentration using a BCA kit (Pierce), and dialyzed overnight at 4° C. (Spectra, 5000 MW cutoff) against PBS. Dialyzed column fractions were then used to coat sterile silicone implants and to inoculate the surgical wound site as described above.

Over Expression and Purification of Recombinant p26

The gene encoding for p29CnB was subcloned into the BamHI-XhoI multicloning site of the bacterial expression vector pET-30 (Novagen, USA). BLR (DE3) competent cells (Novagen, USA) were transformed with the engineered p29CnB-His/pET-30 expression vector. Culture (LB broth+ 30 ug/ml kanamycin) of a p29CnB-His/pET-30 expressing clone was induced to over express the dual His-tagged recombinant protein by the addition of 1 mM IPTG (overnight at 37° C.). The "His-Bind" purification kit from Novagen was used and the manufacturers instructions were followed in order to purify His-tagged recombinant protein. Proteins were removed by centrifugation (30 min, 6000 rpm, Sorvall RC-3B) and collected in the resulting culture media, which contained the sought after secreted recombinant protein. The collected media was then applied to a small polypropylene column containing 2.5 ml of packed, charged (50 mM $NiSO_4$) and equilibrated (binding buffer: 5 mM imidazole, 0.5 M NaCl, 20 mM Tris·HCl pH 7.9) His-Bind resin (Novagen, USA). After an initial wash step with binding buffer the His-tagged protein was eluted using a 20 mM Tris HCl (pH 7.9) buffer containing 0.5 M NaCl and 60 mM imidazole. The eluted fractions were then pooled, dialysed against $dH_2O$, lyopholized and stored at −20° C. Protein purity was analyzed by SDS-PAGE.

Preactivated Surface (PS-1) ProteinChip® Analysis and SELDI-Qq-TOF amino Acid Sequencing of Collagen Binding Proteins Isolated from RC-14

Figure 2:
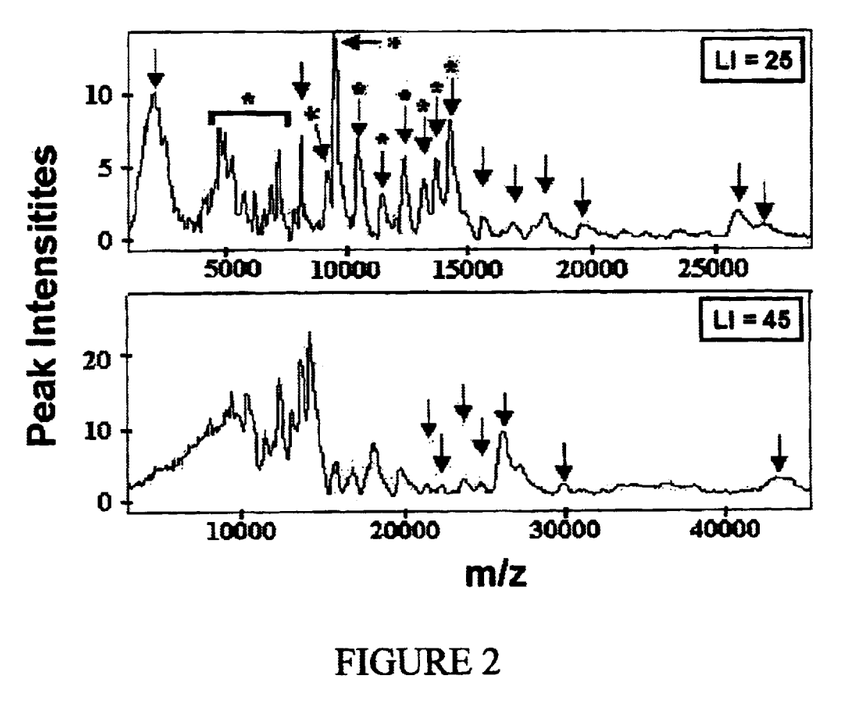
FIG. 2 is a SELDI protein spectrum of the RC-14 biosurfactant that bound to a Cn-III/PS-1 array. Arrows highlight distinct collagen binding peaks. Dual charged peaks (m+2H$^+$) and their potential single charged peaks (m+H$^+$) are bracketed.
Figure 3A:
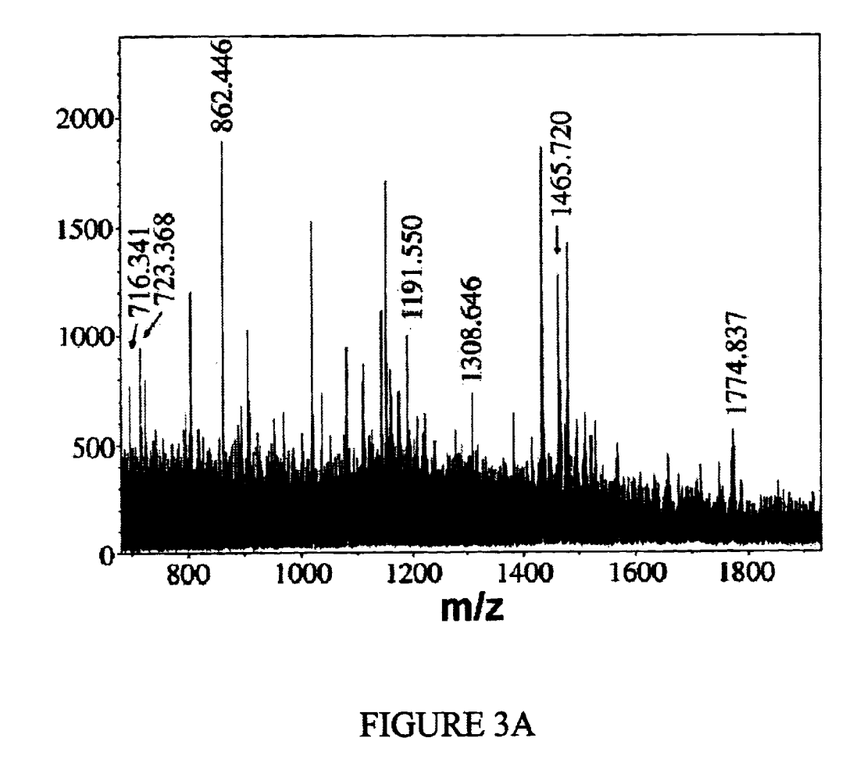
FIG. 3A is a SELDI protein spectrum of the tryptic profiles of collagen binding fractions of L. fermentum RC-14.
Figure 3B:
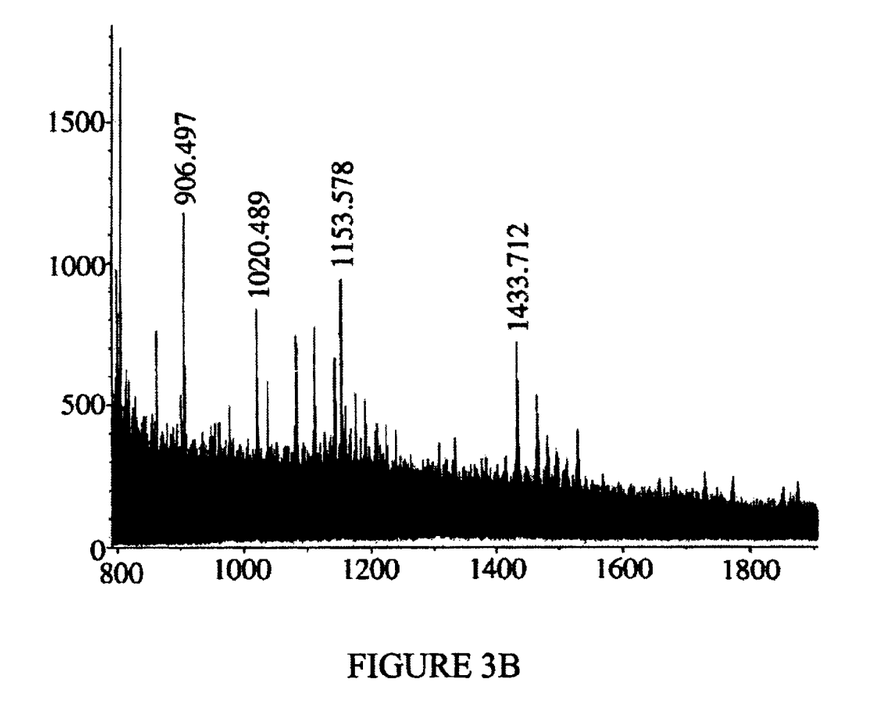
FIG. 3B is a SELDI protein spectrum of the tryptic profiles of collagen binding fractions of L. rhamnosus GR-1.
Figure 3C:
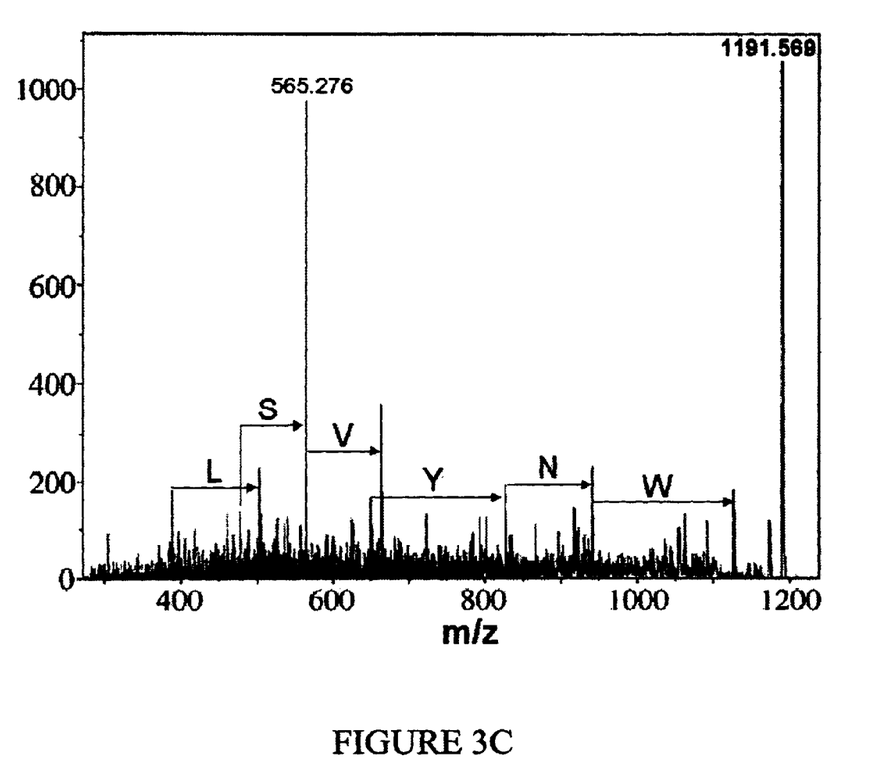
FIG. 3C is a MS/MS spectra of a Lactobacillus biosurfactant peptide derived from L. fermentum RC-14, 1191, 569 Da.
Figure 3D:
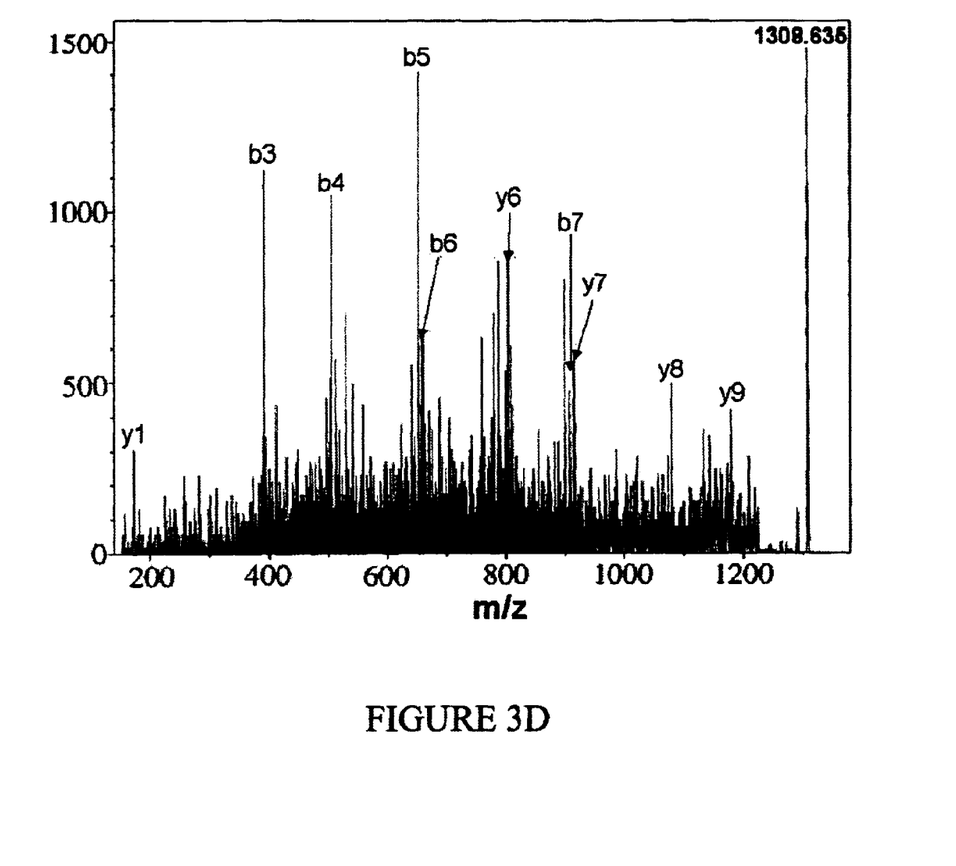
FIG. 3D is a MS/MS spectra of a Lactobacillus biosurfactant peptide derived from L. fermentum RC-14, 1308.635 Da.
Figure 3E:
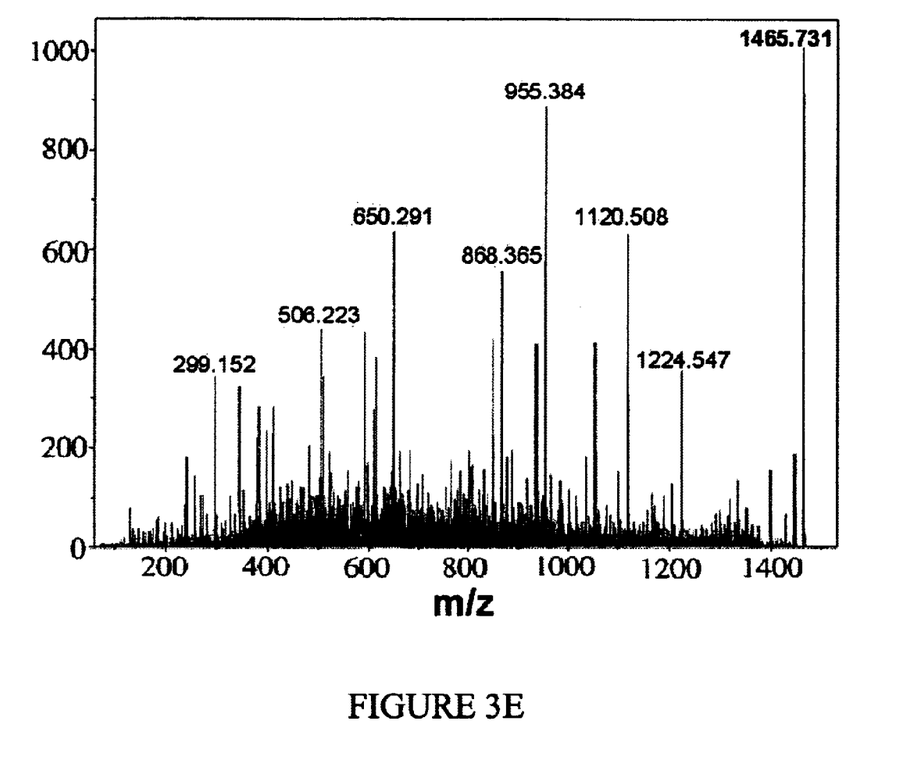
FIG. 3E is a MS/MS spectra of a Lactobacillus biosurfactant peptide derived from L. fermentum RC-14, 1465.731 Da.

Aliquots (2–3 µl) of RC-14 or GR-1 biosurfactants were spotted onto PS-1 ProteinChip® (Ciphergen, Calif.) arrays that contained either immobilized collagen type-I or collagen type-III. The SELDI spectra of the collagen binding proteins was then examined. The biosurfactant proteins bound to each of the spots on the collagen cross-linked PS-1 arrays were then directly subjected to trypsin digestion. The on-chip tryptic digests were then analyzed using a prototype SELDI-interfaced SIEX Q-star. FIGS. 3*a* and 3*b* show the tryptic profiles of the collagen binding fractions of RC-14 and GR-1 biosurfactants respectively, with the labeled peaks being chosen for subsequent MS/MS sequence analysis. Shown in FIGS. 3*c*, 3*d*, 3*e* are the MS/MS spectra of three unique tryptic peptides derived from the RC-14 biosurfactant peptide map (FIG. 2*a*). In total 5 unique peptide sequences were identified using either Cn-I/PS-1 or Cn-III/PS-1 arrays (see Table 1).

EXAMPLE 3

*Lactobacillus fermentum* RC-14 Collagen Binding Activity Inhibited in vivo Implant Infection by *S. aureus*

The ability of lactobacilli biosurfactants to prevent uropathogens from adhering and subsequently infecting healthy human tissue is believed to account, in part, for the beneficial clinical effects of these probiotics. Based on this notion we determined that *Lactobacillus fermentum* RC-14 biosurfactant produces a number of collagen binding proteins using SELDI-TOF-MS (Howard, J., et al. Identification of collagen binding proteins in Lactobacillus using advanced ProteinChip technology. Appl. Environ. Microbiol. In press.). Collagen is a major extracellular matrix (ECM) component of tissues that has also been shown to be an important site of attachment for invading pathogenic bacteria, like *Staphylococcus aureus*.

Figure 1A:
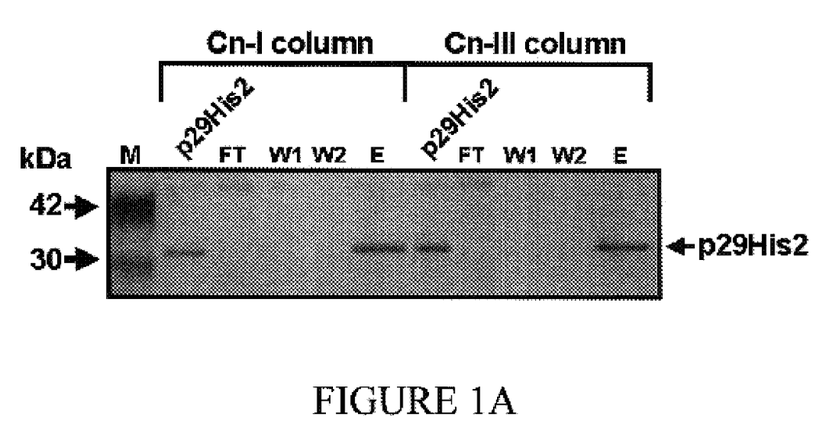
FIG. 1A is a SDS-PAGE gel of the flow through (FT), wash (W) and elution fraction (EF) of the Cn-I and Cn-III affinity columns.
Figure 1B:
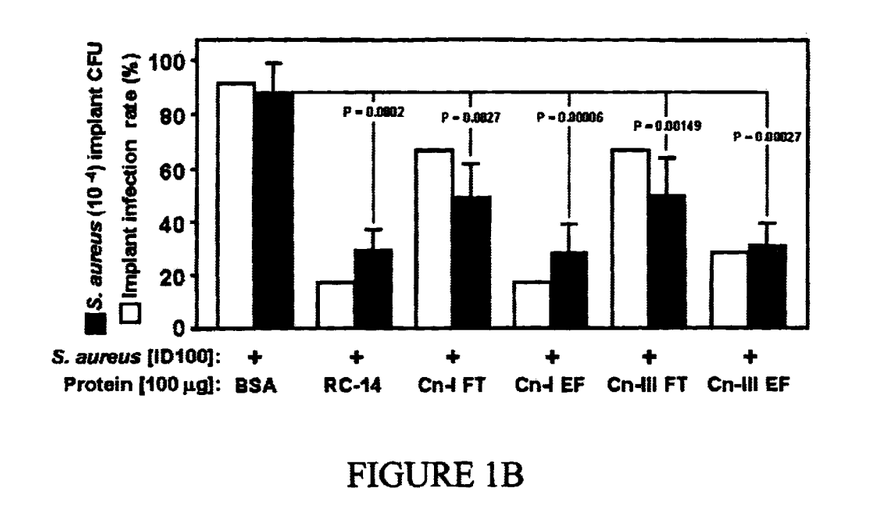
FIG. 1B is a bar graph demonstrating that the collagen binding activity of L. fermentum RC-14 biosurfactant inhibits S. aureus infection and bacterial adhesion to silicone implants in vivo, P=0.0039 (infection rate); P<<0.0001 (Implant CFUs).

To determine whether or not the collective collagen-binding activity of L. fermentum RC-14 may be responsible for its recently discovered anti-infective effects in vivo (U.S. patent application Ser. No. 09/579,306, filed May 25, 2000, incorporated herein by reference), the RC-14 collagen-binding peptides were isolated using a traditional affinity column purification approach. Collagen types I and III were chemically cross-linked to alkylamine beads (Pierce) according to the manufacturers specification. These collagen types were chosen since they are the most common collagens found within the skin. To ensure the effectiveness of the collagen affinity columns, the binding affinity of a recombinant collagen binding protein, p29CnB, which was recently purified from RC-14 biosurfactant was tested first (Heinemann, C., et al. Purification and characterization of a biosurfactant produced by Lactobacillus fermentum RC-14 inhibiting Enterococcus faecalis 1131 adhesion. FEMS Microbiol. Letts. In press.). As shown in FIG. 1a, bacteria were engineered to express a recombinant His-tagged form of p29CnB, which was then purified from the culture media using a $Ni^{+2}$ affinity column (His-Resin kit, Novagen, USA). As shown in FIG. 1a, all 4 mg of the recombinant p29CnB used in the experiment bound very tightly to both Cn-I and CN-III affinity columns, thereby confirming the effectiveness of this purification scheme. Next, the collagen binding peptides from the crude RC-14 biosurfactant were purified and their activity assayed in vivo using the rat surgical implant model. As shown in FIG. 1b, 100 μg of protein eluted from the Cn-I column (Cn-I EF) inhibited S. aureus induced surgical implant infection by 80%, which was the same amount of anti-infection activity observed for crude RC-14 biosurfactant. By comparison, 100 μg of the CN-III elution fraction (CN-III EF) inhibited S. aureus infection by 65%, while the flow through fractions from both types of collagen affinity columns inhibited infection by 20%. In addition, all four column fractions could significantly inhibit the number of S. aureus CFUs that adhered to the surgical implants, when compared to the BSA control treated group (FIG. 1c). However, the most significant anti-adhesive effect was produced by the Cn-I binding fraction of RC-14 biosurfactant, followed by crude RC-14 biosurfactant and the CN-III binding fraction (P=0.00027, P=0.00006, P=0.0002, respectively).

EXAMPLE 4

Identification of RC-14 BSF Collagen Binding Peptides Using PS-1 ProteinChip® Arrays and SELDI-Qq-TOF The RC-14 biosurfactant was screened for peptides possessing collagen-binding activity, using Surface Enhanced Laser Desorption/Ionization time of flight mass spectrometry (SELDI-TOF-MS). Recently, with the aid of this novel ProteinChip® technology (Ciphergen Biosystems, Inc.), it has been demonstrated that RC-14 biosurfactant contains a number of collagen binding proteins and peptides (Howard et al. in press). In an effort to definitively identify these individual collagen-binding proteins and peptides, 'on-chip' protease digest of the partially purified RC-14 biosurfactant was performed, followed by MS-MS sequencing of the peptide fragments using SELDI-Qq-TOF. Binding of either the RC-14 or control GR-1 biosurfactant to PS-1 Protein-Chip® arrays that contain either immobilized collagen type-I or type-III occured first. Shown in FIG. 2a is a typical SELDI protein spectrum of the RC-14 biosurfactant that bound to a Cn-III/PS-1 array. The spectra of the collagen binding proteins for both Cn-I/PS-1 and Cn-III/PS-1 arrays were virtually identical (data not shown). The RC-14 proteins bound to each of the spots on the collagen cross-linked PS-1 arrays were then directly subjected to trypsin digestion. The 'on-chip' tryptic digests were then analyzed using a prototype SELDI-interfaced SIEX Q-star. FIGS. 3a, 3b show the tryptic profiles of the collagen binding fractions of RC-14 and GR-1 biosurfactants, respectively, with the labeled peaks being chosen for subsequent MS/MS sequence analysis. Shown in FIGS. 3c,d,e, are the MS/MS spectra of three unique tryptic peptides derived from the RC-14 peptide map (FIG. 2a). In total 5 novel peptide sequences were identified using either Cn-I/PS-1 or Cn-III/PS-1 arrays (Table 1).

TABLE 1

SELDI-Qq-TOF MS/MS amino acid sequencing of tryptic peptides from Cn-I/PS-1 and Cn-III/PS-1 arrays

| PS-1 array | Tryptic peptide (Da.) | Sequence |
|---|---|---|
| Cn-I/PS-1 | 1. 1465.731 | L^QGLVS[FA]*GSCTCAQK |
|  | 2. 1308.635 | EVYLFQE[QP]R |
|  | 3. 1191.569 | WNYVS |
| Cn-III/PS-1 | 1. 1329.685 | RAFALLSNWPVK |
|  | 2. 1263.696 | GLQGG⁺DL[SH][SH]R |

*[ ] bracketed amino acids indicate the tentative order of the sequence.

^Underlined amino acids indicate likely identities (e.g., M.W. of leucine and isoleucine are the same).

⁺Potentially GG = N (Asparagine) since they have the same molecular weight (M.W.).

What is claimed is:

1. An isolated biosurfactant peptide comprising Glu-Val-Tyr-Xaa$_1$-Phe-Gln-Glu-Xaa$_2$-Xaa$_3$-Arg (SEQ ID NO: 2), wherein Xaa$_1$ is any amino acid and Xaa$_2$ and Xaa$_3$ are selected from the group consisting of Gln or Pro.

2. A pharmaceutical composition comprising the peptide of claim 1, and a pharmaceutically acceptable carrier.

3. A method of treating an infection in a subject, comprising administering to the subject a therapeutically effective amount of the peptide of claim 1 and a pharmaceutically acceptable carrier.

4. A method of inhibiting the binding of a pathogen to a collagen receptor comprising the administration to a subject a therapeutically effective amount of the peptide of claim 1.

5. A method of inhibiting an infection in a subject comprising blocking the interaction of a pathogen with a collagen receptor by the administration of a therapeutically effective amount of the biosurfactant claim 1.

* * * * *